(12) United States Patent
Dolan et al.

(10) Patent No.: US 8,328,867 B2
(45) Date of Patent: Dec. 11, 2012

(54) DRUG LOADED IMPLANTABLE MEDICAL DEVICE

(75) Inventors: Mark Dolan, Santa Rosa, CA (US); Susan Rea, Santa Rosa, CA (US); John Kantor, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 1326 days.

(21) Appl. No.: 11/760,499

(22) Filed: Jun. 8, 2007

(65) Prior Publication Data

US 2008/0306579 A1 Dec. 11, 2008

(51) Int. Cl.
*A61F 2/06* (2006.01)
(52) U.S. Cl. ...................... 623/1.42; 623/1.43
(58) Field of Classification Search ............ 623/1.1, 623/1.15, 1.42, 1.43
See application file for complete search history.

(56) References Cited

U.S. PATENT DOCUMENTS

| | | | |
|---|---|---|---|
| 6,071,305 A | 6/2000 | Brown et al. | |
| 6,254,632 B1 | 7/2001 | Wu et al. | |
| 6,395,326 B1 | 5/2002 | Castro et al. | |
| 6,558,733 B1 | 5/2003 | Hossainy et al. | |
| 6,616,765 B1 | 9/2003 | Castro et al. | |
| 6,638,302 B1 | 10/2003 | Curcio et al. | |
| 6,752,829 B2 | 6/2004 | Kocur et al. | |
| 6,865,819 B2 | 3/2005 | Melittas | |
| 7,055,237 B2 | 6/2006 | Thomas | |
| 7,473,417 B2* | 1/2009 | Zeltinger et al. | 424/78.08 |
| 7,481,835 B1* | 1/2009 | Pacetti et al. | 623/1.15 |
| 2003/0195613 A1 | 10/2003 | Curcio et al. | |
| 2006/0052879 A1 | 3/2006 | Kolb | |

FOREIGN PATENT DOCUMENTS

| | | |
|---|---|---|
| EP | 1393766 | 3/2004 |
| WO | WO2007/087069 | 8/2007 |

* cited by examiner

*Primary Examiner* — Thomas J Sweet
*Assistant Examiner* — Matthew Schall (57) ABSTRACT

A drug eluting implantable device includes an exterior surface on the device and at least one recess formed in the exterior surface. The device further include at least one sidewall protruding from the exterior surface adjacent the at least one recess defining a channel with the recess into which the drug may be loaded, the sidewall including a perpendicular portion substantially perpendicular to the exterior surface and the sidewall further including a parallel portion extending from the perpendicular portion, the parallel portion extending from the perpendicular portion at an angle greater than about 90 degrees as measured with reference to the exterior surface.

12 Claims, 8 Drawing Sheets

DRUG LOADED IMPLANTABLE MEDICAL DEVICE

TECHNICAL FIELD

This invention relates generally to implantable devices that are used for treating vascular conditions and the method of manufacture. More particularly, the invention relates to a device with upstanding walls skived from the surface of the device to deliver a larger amount of the drug and to control the elution rate.

BACKGROUND OF THE INVENTION

Implantable devices are used for a variety of surgical procedures. One such device is a stent. Stents are generally cylindrical shaped devices that are radially expandable to hold open a segment of a blood vessel or other anatomical lumen after implantation into the body lumen to relieve intraluminal constrictions caused by disease or tissue trauma. Although stents alone have been successful in relieving constrictions, these constrictions or blockages reoccur in many cases. This reoccurrence is called restenosis and is due to the body's immune system responding to the trauma of the surgical procedure.

To reduce restenosis, stents have been developed with coatings to deliver drugs or other therapeutic solutions. Once the stent is positioned in a target site, these coatings offer long-term treatment from the drug by a controlled release of a specific amount of the drug from the surface of the stent. The rate of release depends upon the chemical and or biological composition of the drug and the amount of the drug depends upon the total depth and depth consistency of the drug coating layer on the stent surface. It has been discovered that methods of loading drugs onto implantable devices may be deficient in their current drug-loading and drug-delivery characteristics. In particular the amount or volume of the drug capable of being delivered to the target site may be insufficient due to the limited surface areas on the stent and the control of the rate of elution is limited by the chemical characteristics of the drug. In addition, during delivery of the stent, any coating exposed to the body lumen can lose a portion of the coating during delivery, either as a result of bloodflow over the surface, or by contacting the vessel tissue prior to delivery to the target site.

To increase the amount of the drug that may be deposited on the surface of the stent, the surface of the stent framework has been modified. Such modifications may be the formation of openings in the stent surface to hold more of the drug. For example, depots can be formed into the surface of the stent with the use of a multistep chemical etch process or with the use of lasers. However, since the extra amount of drug that can be held in the depots depends directly upon the depth of the depots and an increase in the depth of the depot will reduce the strength and the resiliency of the stent, only a limited extra amount of drug can be placed in the depots. Also the control of the rate of elution is still limited to the chemical characteristics of the drug.

Figure 1:
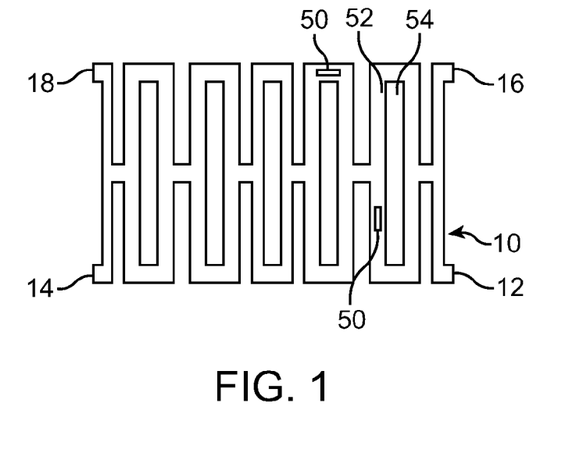
FIG. 1 shows a flat stamped portion of a stent prior to its formation into a cylinder with two channels formed in accordance with the prior art.
Figure 2:
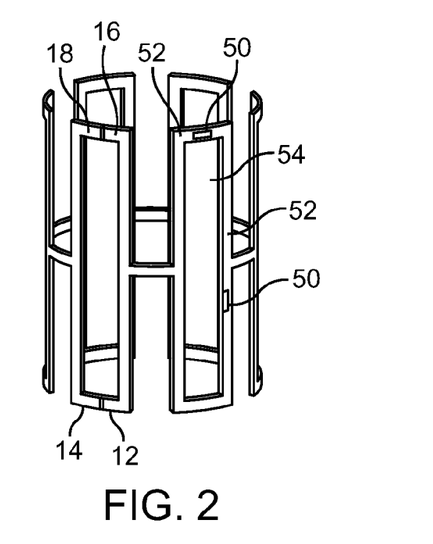
FIG. 2 shows the flat stamped portion of the stent of FIG. 1 bent into a cylindrical stent.
Figures 3, 4:
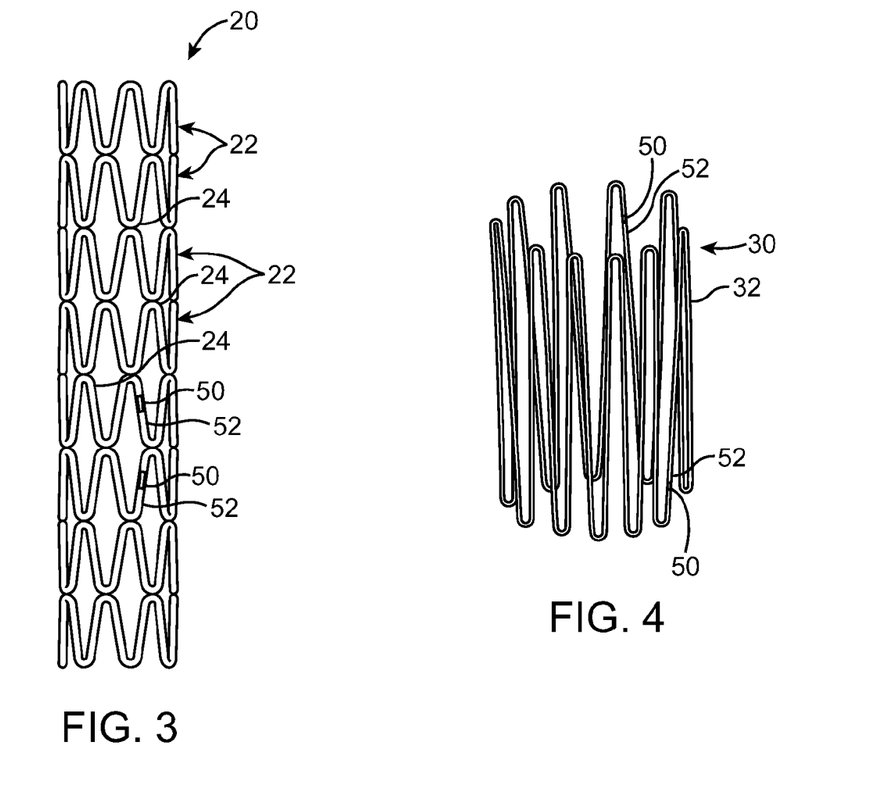
FIG. 3 shows a second type of stent with two channels formed in accordance with the prior art.
FIG. 4 shows a third type of stent with two channels formed in accordance with the prior art.

Various types of stents are currently in use. FIGS. 1-4 illustrate stent portions in common use. Each of the illustrated stents suffer from undesirably limited surface area on the stent for the placement of a drug coating or for the placement of openings in the narrow remaining areas of the stents called struts. Also, removal of a portion of stent struts, such as to form openings in the surface to contain an additional amount of the drug, can undesirably limit the strength or resiliency of the stent being so machined. Each of the stents in FIGS. 1-4 have two channels 50 formed in struts 52 made in accordance with this invention into which a drug can be loaded. FIG. 1 illustrates a stent 10 stamped from a flat sheet of metal having ends 12, 14, 16, and 18. FIG. 2 shows the stamped flat sheet after being bent into a cylinder with ends 12 and 14 and 16 and 18 respectively being joined to hold the flat sheet in a cylindrical shape. FIG. 3 shows a stent 20 formed by joining a plurality of stamped rings 22 in which rings are bent into a sinusoidal form. Some of the points 24, which are defined as a peak deviation from the centerline of the sinusoidal ring, are joined together to fasten segments 22 which form the stent. Finally, stent 30, shown in FIG. 4, is formed from a wire 32 or a plurality of wires 32 that are bent to form the stent. The surface area onto which the drug can be loaded and each strut 52 is limited so that a channel with a very large depth will reduce the strength or resiliency of the stent.

Formation of surface modifications can reduce structural integrity due to loss of material during manufacture. It is desirable, in certain applications, to increase structural integrity. In addition, handling and packaging of drug loaded stents is complicated by the presence of the drug on the stent. For example, frictional contact with a surface, such as during packaging or shipping, can abrade at least a portion of the drug from the stent surface. Furthermore, certain treatments are better obtained by reducing elution of the drug from the stent during traversal of vasculature.

It would be desirable, therefore, to advance the art.

SUMMARY OF THE INVENTION

One aspect of the present invention is a drug eluting implantable device that includes an exterior surface on the device and at least one recess formed in the exterior surface. The device further includes at least one sidewall protruding from the exterior surface adjacent the at least one recess defining a channel with the recess into which the drug may be loaded, the sidewall including a perpendicular portion substantially perpendicular to the exterior surface and the sidewall further including a parallel portion extending from the perpendicular portion, the parallel portion extending from the perpendicular portion at an angle greater than about 90 degrees as measured with reference to the exterior surface.

Another aspect of the invention provides a system for treating a vascular condition. The system comprises a catheter and a stent carried on the catheter. The stent includes an exterior surface on the device, at least one recess formed in the exterior surface, and at least one sidewall protruding from the exterior surface adjacent the at least one recess defining a channel with the recess into which the drug may be loaded. The sidewall includes a perpendicular portion substantially perpendicular to the exterior surface and the sidewall further includes a parallel portion extending from the perpendicular portion, the parallel portion extending from the perpendicular portion at an angle greater than about 90 degrees as measured with reference to the exterior surface.

Another aspect of the invention provides a method of forming a drug carrying device. The method includes receiving a medical device for implantation within a body lumen and skiving at least a first recess on an exterior surface of the medical device. The method further includes forming at least one first sidewall based on the skiving, each first sidewall protruding from the exterior surface substantially perpendicularly; and swaging the at least one formed first sidewall to form a parallel portion extending from the perpendicular portion, the parallel portion extending from the perpendicular portion at an angle greater than about 90 degrees as measured with reference to the exterior surface.

The foregoing and other features and advantages of the invention will become further apparent from the following detailed description of the preferred embodiments, read in conjunction with the accompanying drawings. The detailed description and drawings are merely illustrative of the invention, rather than limiting the scope of the invention being defined by the appended claims and equivalents thereof.

DETAILED DESCRIPTION OF THE PREFERRED EMBODIMENT

Use of the disclosures and teachings herein provides for construction of a stent that includes at least one recessed channel that is at least partially encapsulated by a skived sidewall to protect encapsulated therapeutic agents during delivery to the target site. In addition, the machining of the stent to form the encapsulating surfaces occurs after application of the therapeutic agent to the stent.

Figure 5A:
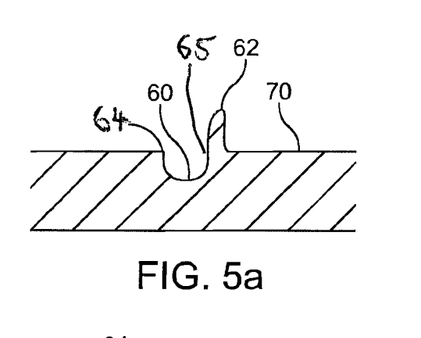
FIG. 5a illustrates a channel formed in the exterior surface of a stent including a sidewall protruding from the surface, in accordance with one aspect of the invention.
Figure 5B:
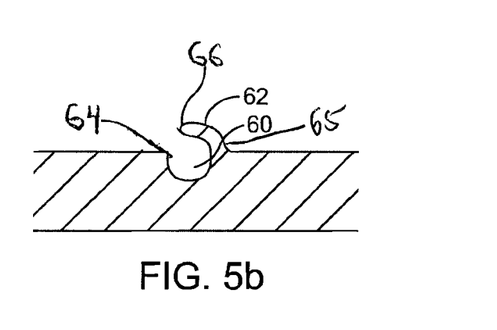
FIG. 5b illustrates the channel of FIG. 5a with the sidewall bent over the channel, in accordance with one aspect of the invention.

FIG. 5A illustrates a cross section of an exterior surface of a device 500, in accordance with one aspect of the invention. In one embodiment, device 500 is a stent. Device 500 includes a surface 70 and a channel 60. Channel 60 is defined by first sidewall 62 and second sidewall 64. First sidewall 62 protrudes above surface 70 and includes perpendicular portion 65. FIG. 5B illustrates the device 500, with first sidewall 62 bent into a final form. When bent, first sidewall includes the perpendicular portion 65 and a parallel portion 66 extending from the perpendicular portion 65. The parallel portion 66 extends from the perpendicular portion 65 at an angle greater than about 90 degrees as measured with reference to the exterior surface 70. Thus, the parallel portion covers at least a portion of the recess. In one embodiment, a therapeutic agent is disposed within the recess. The therapeutic agent is disposed within the recess prior to bending the sidewall via a cold machining process, such as swaging. The parallel portion, in one embodiment, is substantially parallel to a lower surface of the recess. In yet another embodiment, the parallel portion includes an end portion which is further bent down, such that the angle defined by the end portion with reference to the surface exceeds 135 degrees, so that any edge or point is directed toward the body of the device, rather than away from the surface. In one embodiment, first sidewall 62 is formed as the result of a skiving operation such that the sidewall is formed of material skived from the surface to form the recess.

Figure 6A:
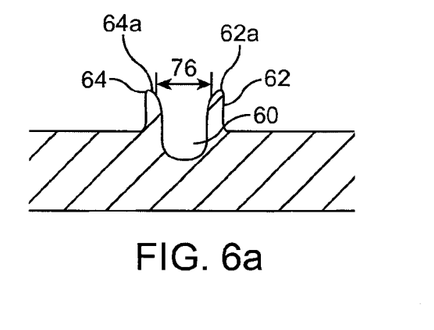
FIG. 6a illustrates a channel formed in the exterior surface of a stent including a first sidewall protruding from the surface and a second sidewall protruding from the surface, in accordance with one aspect of the invention.
Figure 6B:
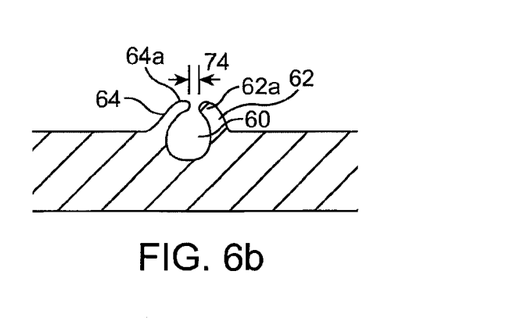
FIG. 6b illustrates the channels of FIG. 6a with the first sidewall bent over the channel and the second sidewall bent over the channel, in accordance with one aspect of the invention

FIG. 6A illustrates a cross section of an exterior surface of a device 600, in accordance with one aspect of the invention. FIG. 6A is similar to FIG. 5A, with the addition that second sidewall 64 extends or protrudes above the surface 70, as well as first sidewall 62. FIG. 6A further illustrates that the first sidewall and second sidewall further define a recess width 76. FIG. 6B illustrates the first sidewall and second sidewall bent over towards each other, such that the end portion of the first sidewall points toward the end portion of the second sidewall, and the end portion of the second sidewall points toward the end portion of the first sidewall. The width of the channel 60 defined by the first sidewall and second sidewall is larger near the lower surface of the recess than the width 74 at the end portion of the first sidewall and second sidewall.

Figure 7A:
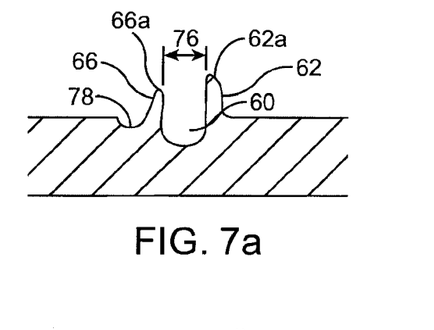
FIGS. 7a and 7b show a cross section of two channels formed in the exterior surface of a stent with one upstanding wall formed from material skived from the recess and with the same the other upstanding wall formed from material in the exterior surface not from the recess and with the same two upstanding walls but with only one bent, in accordance with one aspect of the invention.
Figure 7B:
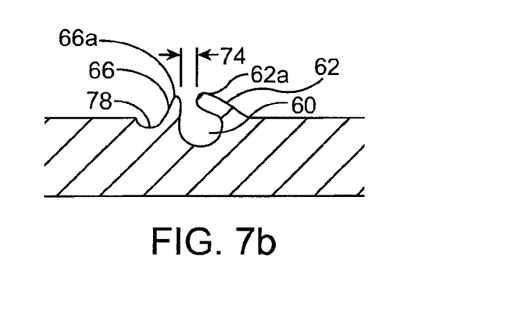

FIG. 7A and FIG. 7B illustrate that the first sidewall and second sidewall can have different lengths such that second sidewall 64 does not protrude from the surface 70 the same distance as first sidewall 62.

Figure 8:
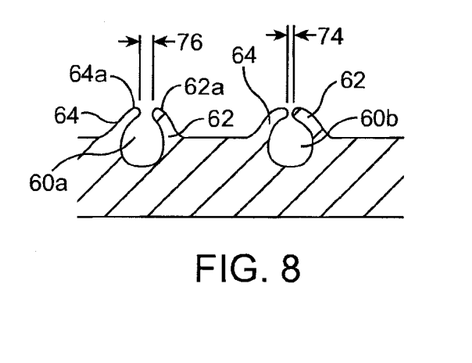
FIG. 8 shows a cross section of two channels formed in the exterior surface of the stent each channel with two upstanding walls bent toward each other where the tops of the walls define an opening and the opening dimension of one channel being different from the opening dimension of the other channel, in accordance with one aspect of the invention.

FIG. 8 illustrates that numerous channels, such as the two channels 60a and 60b, can be produced within the body of the device. Each channel 60a, 60b is defined by a recess and two upstanding walls where the upstanding walls from a respective channel are bent a different amount creating openings which are spaced apart with different opening dimensions. The opening dimension 76 between distal ends 62a and 64a of channel 60a is larger than the opening dimension 74 between distal ends 62a and 64a of channel 60b. In one embodiment, the therapeutic agent placed within channel 60*a* is different than the therapeutic agent placed in other channel 60*b*. In one embodiment, the therapeutic agent placed within channel 60*a* is the same as the therapeutic agent placed in other channel 60*b*. For example, the drug placed within channels of differing physical characteristics can be selected.

In one embodiment, the different opening dimension between the distal ends of the upstanding walls results in different elution rates. The elution rate from channel 60*a*, in one embodiment, is greater than the elution rate from channel 60*b*. By varying the opening dimension, the elution rate of a drug in a channel can be controlled. For example, a first drug, which may be needed shortly after stent placement, can be loaded in channel 60*a*, which has a larger opening dimension and, therefore, will allow for a higher elution rate. A second drug, which may be needed for a longer period of time and after the initial stent placement, can be loaded in channel 60*b*, which has a smaller opening distance and, therefore, will allow for a lower elution rate.

Figure 9:
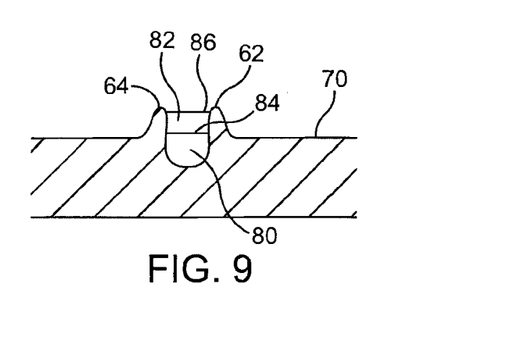
FIG. 9 shows a cross section of a channel formed in the exterior surface of the stent where a second drug is placed on top of a first drug in the channel and also shows the extra amount of drug that can be filled in the channel with upstanding walls, in accordance with one aspect of the invention.

FIG. 9 illustrates first therapeutic agent 80 disposed within channel 60. In addition, FIG. 9 illustrates second therapeutic agent 82 disposed above first therapeutic agent 80. The invention can be practiced with a single layer of therapeutic agents.

Figure 10:
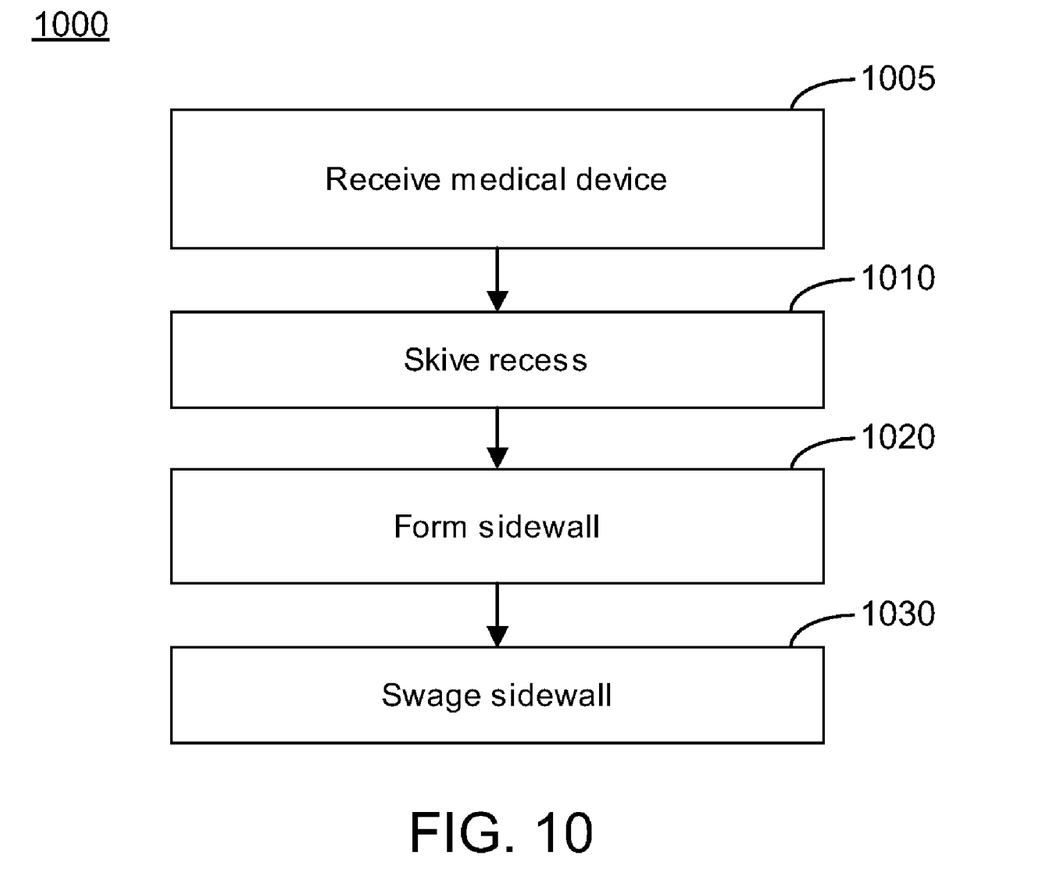
FIG. 10 illustrates a flowchart representative of a method for forming a medical device, in accordance with one aspect of the invention.

FIG. 10 is a flowchart of a method 1000 for forming a drug carrying device, in accordance with one aspect of the invention. Method 1000 begins at step 1005 by receiving a medical device for implantation within a body lumen. In one embodiment, the medical device is a stent. At least a first recess is skived on an exterior surface of the medical device at step 1010. This skiving forms, step 1020, a first sidewall, such as first sidewall 62, protruding from the exterior surface, substantially perpendicular to the exterior surface. The medical device is then swaged, including swaging, step 1030, the at least one formed first sidewall to form a parallel portion extending from the perpendicular portion, the parallel portion extending from the perpendicular portion at an angle greater than about 90 degrees as measured with reference to the exterior surface. In one embodiment, the method further includes applying at least one therapeutic agent to the recess prior to swaging the formed sidewall. Those of skill in the art will recognize that the cold forming swaging technique can reduce degradation of the therapeutic agent that could result from heat treatments.

In another embodiment, the method further includes skiving at least one second sidewall on the exterior surface, such that the second sidewall is separated from the first sidewall by the recess and connected to the first sidewall via a lower surface of the recess, each first sidewall protruding from the exterior surface substantially perpendicularly. In this embodiment, the method further includes swaging the second sidewall to form a parallel portion extending from the perpendicular portion, the parallel portion extending from the perpendicular portion at an angle less than about 90 degrees as measured with reference to the exterior surface.

The method of forming the stent with upstanding walls can include stamping the struts of the stent while skiving the upstanding walls to form the recess in the same process. A multi station die set can first stamp the cut out. In the next die station the recess and upstanding wall or walls can be initially swaged from the surface. In a subsequent or final die station, the recess and upstanding wall or walls can be formed into their final shapes. In a further modification another die station can be provided which can also bend the upstanding wall or walls to form the predetermined opening between the distal ends of the upstanding wall or walls. Other methods can be used to form the recesses and upstanding walls. For example, a preformed stent can be placed on a holding mandrel and the stamping operation as described above can be used to form the recesses and upstanding walls. Other methods can include the use of a laser or a water cutting process to form the recesses and upstanding walls.

In one embodiment, the stent framework is formed from bioerodable and/or bioabsorbable materials, such as magnesium, or certain polymers. In such embodiments, the skived channels and the gap defined by the sidewalls are configured to create a channel or other such recess that accelerates the dissolution of the stent framework after a span of time or previous erosion. For example, a topcoat is applied over a stent framework to provide for a first rate of elution or dissolution. As the topcoat elutes from the stent framework at the first rate, the recess is exposed to the vessel environment, and the therapeutic agent disposed within the recess will elute, for example at a second rate of elution. The first and second rates of elution may be different or the same. In addition, the bioabsorbable stent framework will elute, at a third rate of elution. The rates of elution can be controlled to provide for accelerating (or decelerating as desired) dissolution.

In another embodiment, the stent framework is formed of bioerodable and/or bioabsorbable materials, and a hydroactive solution is maintained within the channels. A topcoat surrounds the framework, and maintains the hyrdoactive solution within the channels. As the topcoat leaches or elutes off the framework, the hydroactive solution is exposed to the vessel environment, and accelerates the erosion/absorption of the stent framework. In one embodiment, the hydroactive solution produces an exothermic reaction upon contact with blood. Alternatively, the hydroactive solution can produce an exothermic reaction based on exposure to another solution applied to the stent framework, such as a saline solution delivered via a catheter. In one embodiment, the hydroactive solution is hydrophilic.

In certain embodiments, the recesses described herein are provided in the inner diameter of the lumen defined by the framework. Such embodiments are generally implemented for distribution of a therapeutic agent intended for direct administration within the blood stream, rather than to the intima surrounding the stent. In yet other embodiments, the recesses described herein can be provided in the sidewalls of the stent framework so that the portion of the sidewall extending above the exterior surface does not impact the intima or extend into the lumen defined by the stent framework.

Figure 11:
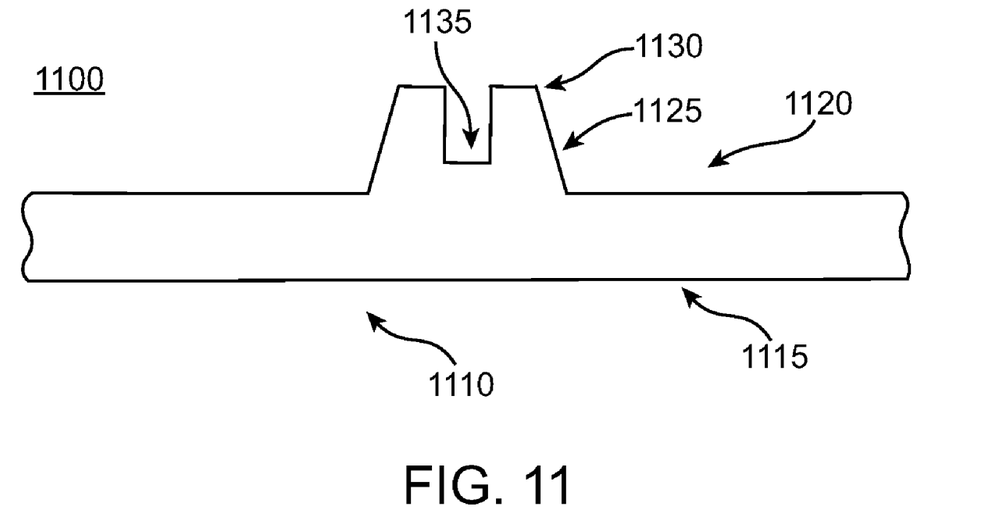
FIG. 11 illustrates a profile of a depot in accordance with one aspect of the invention.
Figure 12:
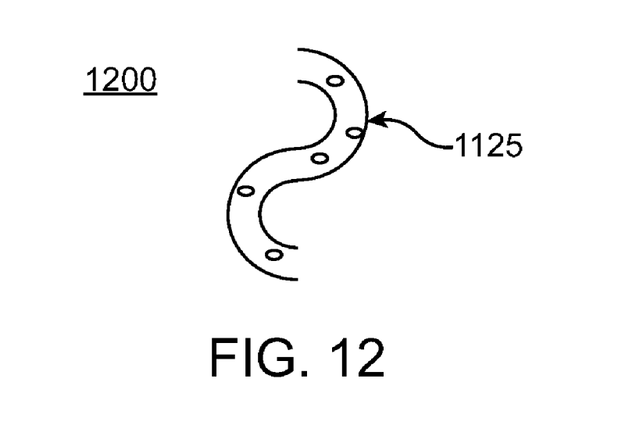
FIG. 12 illustrates a perspective view of a stent strut including depots in accordance with one aspect of the invention.

FIG. 11 illustrates one embodiment of a drug eluting implantable device 1100 in accordance with one aspect of the invention. Device 1100 includes a framework comprising at least one stent wire 1110. The stent wire 1110 includes an inner surface 1115 defining a lumen and at least one outer surface 1120 opposing the inner surface 1115. At least one depot 1125 is disposed on at least a portion of the outer surface 1120. Depot 1125 includes at least one wall portion 1130 defining an axis offset from the outer surface. In one embodiment, depot 1125 includes a base surface 1135 substantially parallel with the outer surface 1120. In another embodiment, depot 1125 includes a base surface offset from the outer surface. In one embodiment, the depot includes at least a first outer wall portion connected to the outer surface and a depot wall portion connected to the base surface, such that the first outer wall portion extends a greater distance than the depot wall portion. In one embodiment, the depot includes at least a first outer wall portion connected to the outer surface and a depot wall portion connected to the base surface, such that the first outer wall portion extends a lesser distance than the depot wall portion. In one embodiment, depot 1125 is formed as an integral portion of the stent wire. In another embodiment, depot 1125 is formed as a separate structure and affixed to the outer surface. In one embodiment, the formed stent attains a 'studded' appearance such that the depots extend away from the lumen of the stent and extend beyond the space defined by the stent wire. In one embodiment, depot 1125 is filled with at least one therapeutic agent prior to delivery to a target site within a vessel. FIG. 12 illustrates a portion of a stent framework including a plurality of depots 1125 disposed on the outer surface of the stent wire.

Figure 13:
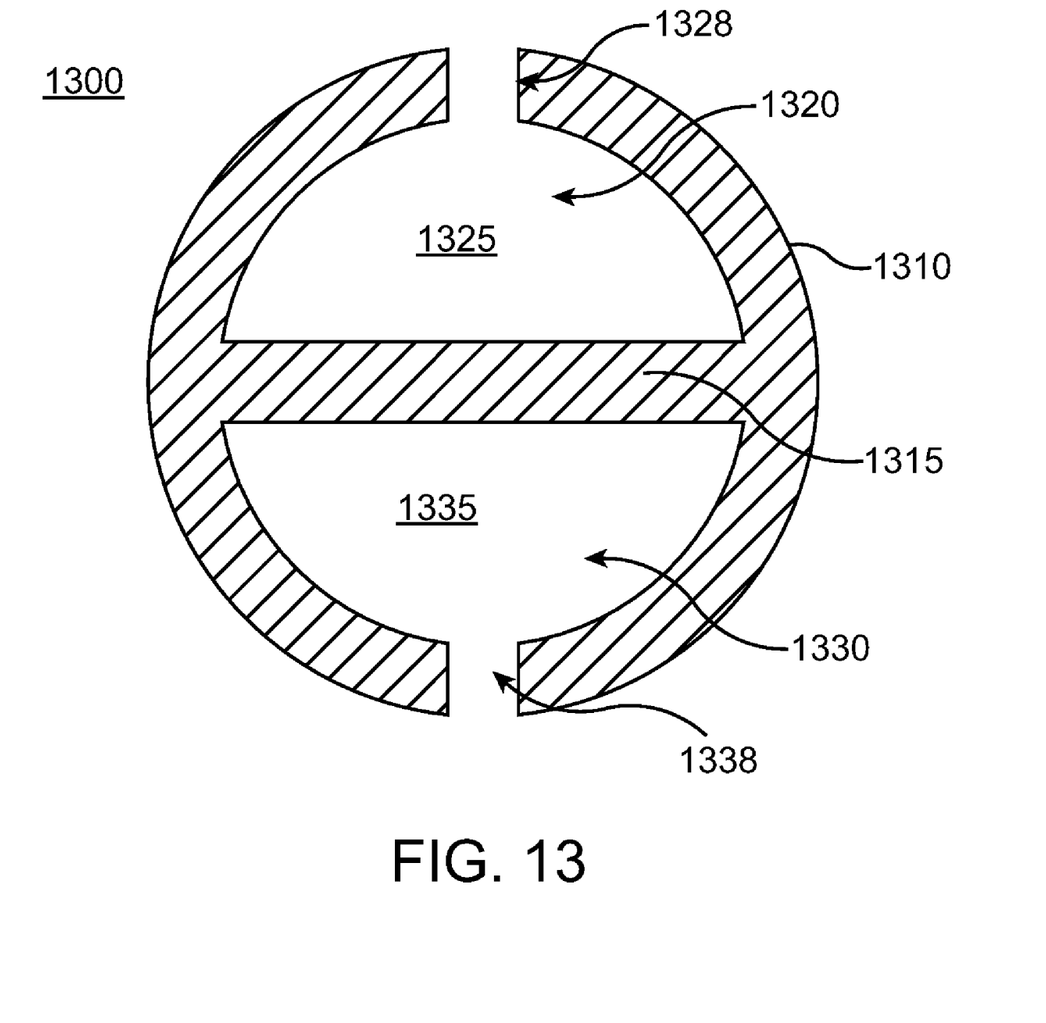
FIG. 13 illustrates one embodiment of a stent in accordance with one aspect of the invention.

FIG. 13 illustrates a cross section of a drug eluting implantable device 1300 in accordance with another aspect of the invention. Device 1300 includes a stent wire 1310 including a first axial chamber 1320 and a second axial chamber 1330. Wall 1315 separates first axial chamber 1320 from second axial chamber 1330. First aperture 1328 provides fluid communication between first axial chamber 1320 and the ambient environment, such as a vessel wall. Second aperture 1338 provides communication between second axial chamber 1330 and the ambient environment, such as a blood stream. First drug 1325 is disposed within first axial chamber 1320 and second drug 1335 is disposed within second axial chamber 1330, such that first drug 1325 and second drug 1335 elute through the first aperture 1328 and second aperture 1338 to attain therapeutic effects. First drug 1325 and second drug 1335 are not the same drug. In one embodiment, first drug 1325 is an anti-restenotic drug, such as ABT-578, marketed as ZOTAROLIMUS. In another embodiment, first drug 1325 is a combination of at least two drugs. In one such embodiment, first drug 1325 includes ZOTAROLIMUS and FLUOCINOLONE. In yet another embodiment, first drug 1325 is a combination of anti-proliferative and anti-inflammatory drugs. In embodiments featuring a combination of drugs, the drugs may be mixed together, or layered within the axial chamber to control for elution patterns. Thus, in one embodiment, the drug burst profile through the implantable device 1300 can be controlled such that a drug affecting early cell response is released prior to a drug affecting longer-term cell response. In other embodiments, the size of the apertures 1328, 1338 are controlled to affect elution rates. In such embodiments, either the depth or the diameter, or both, can be controlled to affect elution rates in a desired fashion. In one embodiment, second drug 1325 is an anti-thrombotic agent, such as plavix.

Figure 14:
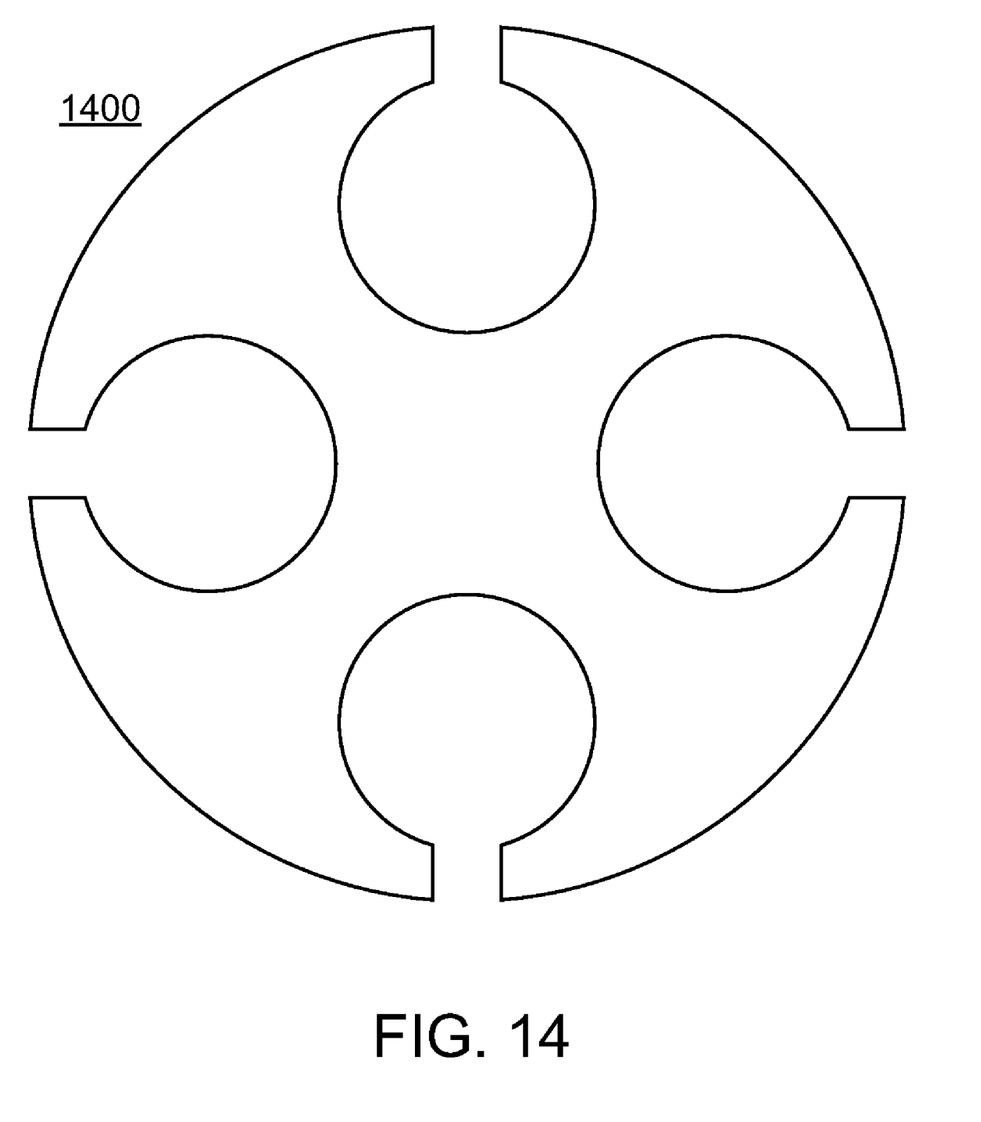
FIG. 14 illustrates one embodiment of a stent in accordance with one aspect of the invention.

FIG. 14 illustrates a cross section of drug eluting implantable device 1400 in accordance with one aspect of the invention. Device 1400 includes a stent wire 1405 including a first axial chamber 1410, a second axial chamber 1420, a third axial chamber 1430, and a fourth axial chamber 1440. Wall 1415 separates first axial chamber 1410, second axial chamber 1420, third axial chamber 1430, and fourth axial chamber 1440. A plurality of apertures provides fluid communication between the axial chambers and ambient environment, such as a vessel wall or blood stream. Different drugs are disposed within each of the axial chambers, in one embodiment. For example, an anti-restenotic drug is disposed in one of the axial chambers, while an anti-thrombotic agent is disposed in another axial chamber. The apertures can be formed using appropriate techniques, such as drilling, forming, skiving, and/or cutting. In addition, in one embodiment, the apertures are further swaged after any cutting procedure.

Figure 15:
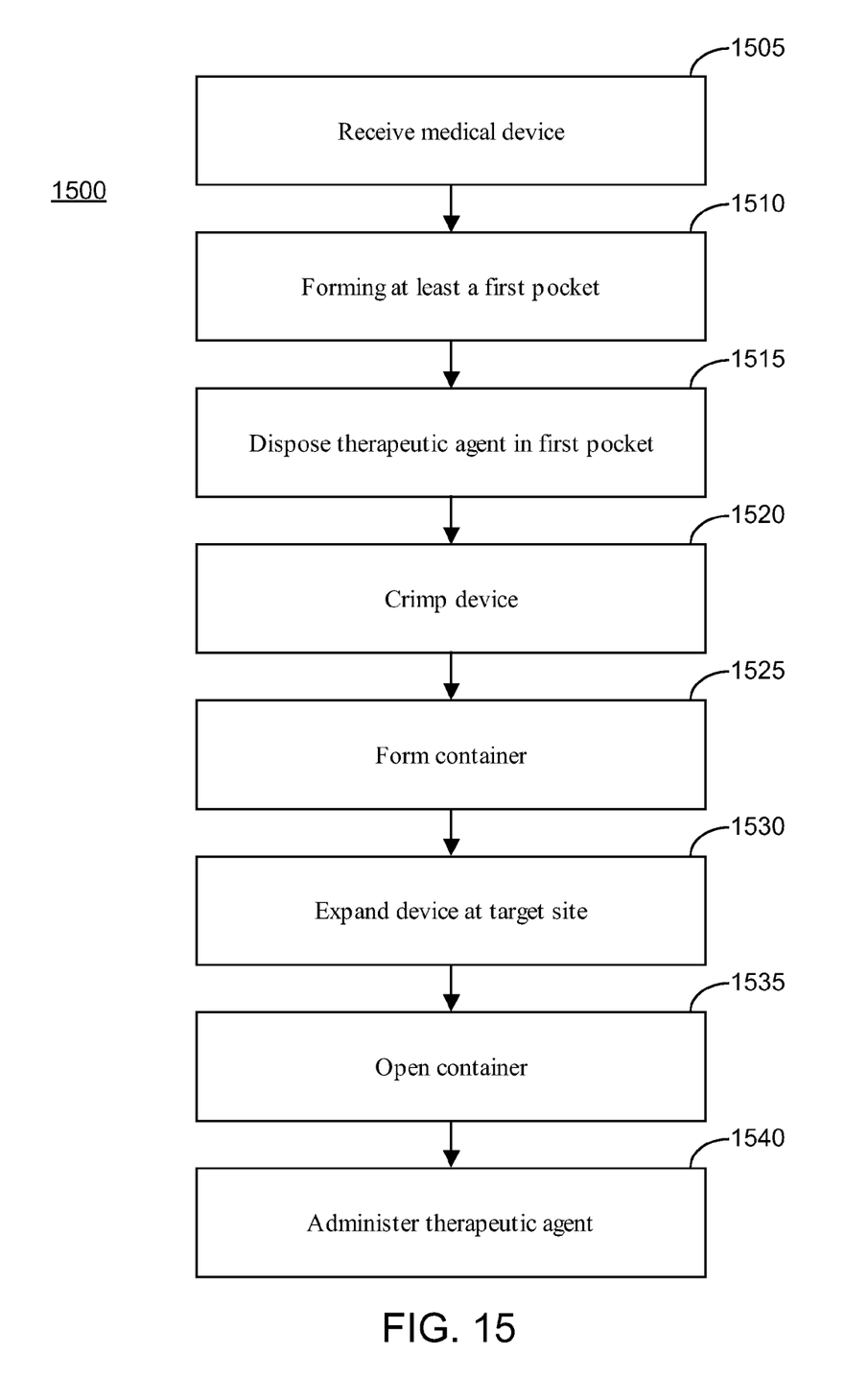
FIG. 15 illustrates one embodiment of a method, in accordance with another aspect of the invention.

FIG. 15 illustrates one embodiment of a method 1500 for administering a therapeutic agent at a target site in accordance with one aspect of the invention. Method 1500 begins by receiving a medical device for implantation in a body lumen at step 1505. At least a first pocket including an opening is formed on an exterior surface of the medical device at step 1510. In one embodiment, a stent wire is extruded with pockets formed in at least one surface of the stent wire. In one embodiment, the pocket is formed on a surface opposing a lumen of the device. In other embodiments, the pocket is formed on a side surface, such as a surface near an adjacent structure. For example, in embodiments wherein the device is a stent, the pocket is formed on a side adjacent the adjoining stent strut. In one such embodiment, each stent strut is formed with a first side surface configured to mate with a second side surface of the adjoining stent strut, while leaving a pocket space open for receiving a therapeutic agent. In one such embodiment, one stent strut assumes a concave profile matched to a convex profile of the mating surface of the adjoining stent strut. At least one therapeutic agent is disposed within the first pocket at step 1515, and the device is crimped with the therapeutic agent disposed within the first pocket at step 1520. In one embodiment, the device is crimped to a balloon catheter.

Step 1525 forms a container from the pocket based on the crimping with at least a portion of the therapeutic agent disposed within the container. The device is expanded at the target site at step 1530, and the container is opened based on the expansion at step 1535. The therapeutic agent is then administered at the target site responsive to the opened container at step 1540. In one embodiment, the therapeutic agent elutes out of the opened container.

Using method 1500, a pocket is formed on an implantable medical device, such as a stent. The pocket is at least partially filled with a therapeutic agent, and the pocket is closed to form a container, at least partially surrounding the therapeutic agent. In one embodiment, the closing results from crimping the device to a delivery device, such as a catheter. Then, upon expansion of the device at a target site, the pocket is reopened, allowing the therapeutic agent within the pocket to be administered at the site. In one embodiment, the crimping pushes an adjacent strut of the stent into the pocket, covering the opening, and the opening is uncovered when the stent is expanded during deployment. In one embodiment, primary drug elution does not occur until the stent is positioned at a deployment or target site, and the stent is deployed to open the container. While a portion of the drug may elute during traversal of the vasculature, this premature elution is reduced by reducing the proportion of drug exposed to the environment within the vasculature until the stent reaches the target site to specifically target the therapeutic site. In one embodiment, this reduced elution provides for an improved estimate of the correct dosage or level of therapeutic agent since less of the drug will prematurely elute. In addition, since the drug is primarily encased within the container during sterilization, packaging, and shipping, a lower fraction of the drug will abrade from the stent surface, further allowing greater precision in dosage of the therapeutic agent. In certain instances, this lower fraction can provide for applying less volume of therapeutic agent to the stent, simultaneously reducing the cost of the therapeutic agent and increasing dosage accuracy.

Figure 16:
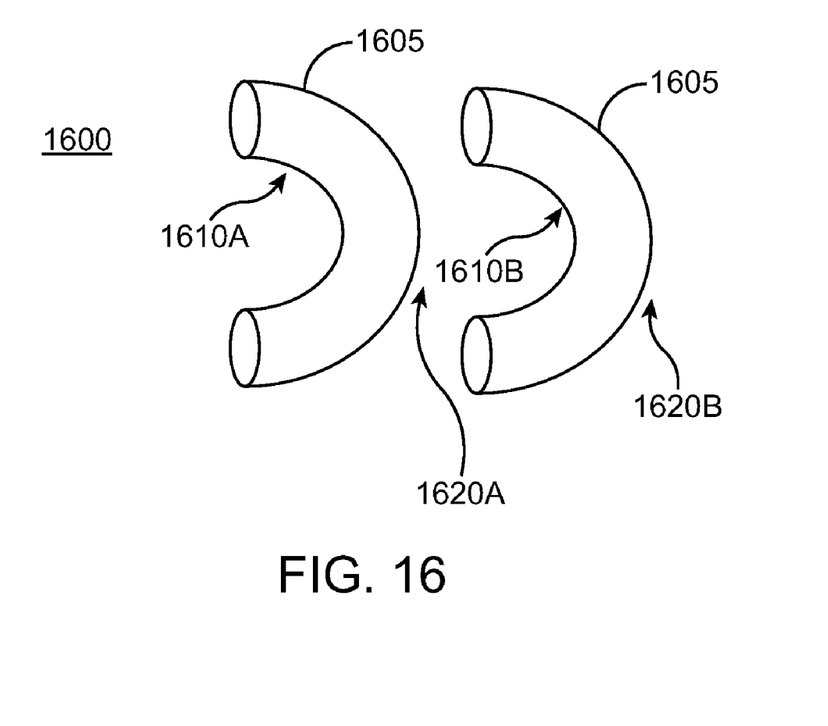
FIG. 16 illustrates one embodiment of a stent wire in accordance with one aspect of the invention.
Figure 17:
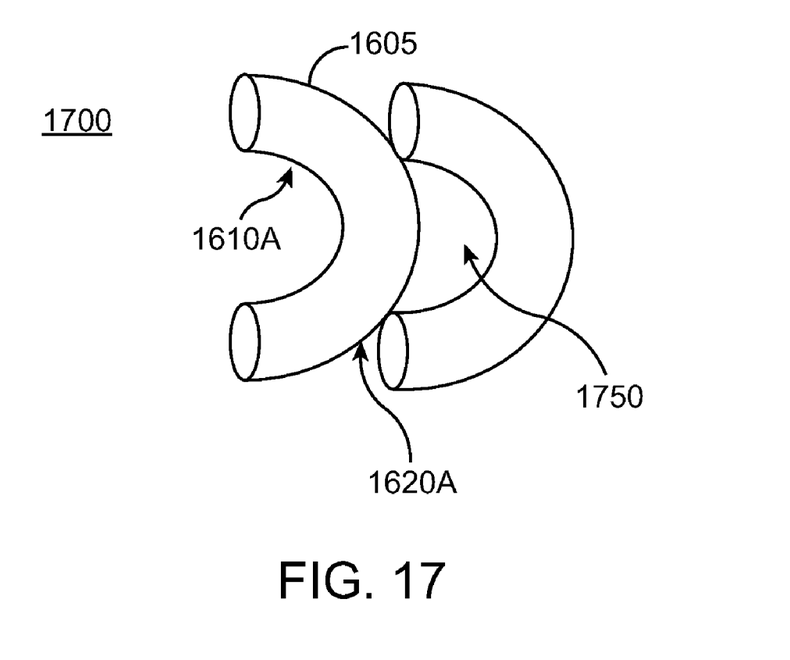
FIG. 17 illustrates one embodiment of a stent wire in accordance with one aspect of the invention.

FIG. 16 illustrates one embodiment of a partial cross section of two adjacent stent wires 1605, in accordance with one aspect of the invention. Each stent wire includes a pocket 1610A, 1610B formed on a lateral surface of the stent wire and a surface 1620A, 1620B to mate with the pocket 1610A, 1610B of the adjacent stent wire. FIG. 16 illustrates the adjacent stent wires separated from each other, in a configuration either before crimping, or after deployment. In contrast, FIG. 17 illustrates the same stent wires in a crimped position, such that pocket 1610B and surface 1620A define a container 1750. When in the configuration illustrated in FIG. 16, a therapeutic agent can be disposed within the pocket 1610B and trapped within a container 1750 when crimped, such as to a catheter.

As used herein, the term "therapeutic agent" includes any pharmaceutically active substance, either alone, or in combination with a polymer carrier. In addition, the term "therapeutic agent" can include various solvents or other substance to either affect elution of the substance, or to enhance adhesion of the therapeutic agent to the surface. The therapeutic agent can be, for example, an antirestenotic agent such as rapamycin, a rapamycin derivative, or a rapamycin analog to prevent or reduce the recurrence of narrowing and blockage of the bodily vessel. Alternatively, the therapeutic agent can be an anti-cancer drug such as camptothecin or other topoisomerase inhibitors, an antisense agent, an antineoplastic agent, an antiproliferative agent, an antithrombogenic agent, an anticoagulant, an antiplatelet agent, an antibiotic, an anti-inflammatory agent, a steroid, a gene therapy agent, an organic drug, a pharmaceutical compound, a recombinant DNA product, a recombinant RNA product, a collagen, a collagenic derivative, a protein, a protein analog, a saccharide, a saccharide derivative, a bioactive agent, a pharmaceutical drug, a therapeutic substance, or a combination thereof. The therapeutic agent constituency in the drug layers may be, for example, between 0.1 percent and 50 percent of the drug layer by weight. In other examples, the therapeutic agent is 100% of the drug layer by weight. In another example, the therapeutic agent comprises an anti-proliferative compound such as 5-fluorouracil, with an optional second therapeutic agent such as rapamycin, a rapamycin derivative, a rapamycin analog, or dexamethosone. In another example, the first therapeutic agent comprises an anti-inflammatant such as dexamethasone, and an optional second therapeutic agent such as 5-fluorouracil.

The skiving processes disclosed herein, in one embodiment, are implemented with a laser cutting tool. In one embodiment, the laser cutting tool is operated out of focus to result in a rougher cut than a focused tool could provide.

It is important to note that the figures herein illustrate specific applications and embodiments of the present invention, and are not intended to limit the scope of the present disclosure or claims to that which is presented therein. Upon reading the specification and reviewing the drawings hereof, it will become immediately obvious to those skilled in the art that many other embodiments of the present invention are possible, and that such embodiments are contemplated and fall within the scope of the presently claimed invention without departing from the spirit and scope of the invention. The scope of the invention is indicated in the appended claims, and all changes that come within the meaning and range of equivalents are intended to be embraced therein.

We claim:

1. A drug eluting implantable device comprising:
an exterior surface on the device;
at least one recess formed in the exterior surface; and
at least one sidewall protruding from the exterior surface adjacent the at least one recess defining a channel with the recess into which the drug may be loaded, the sidewall including a perpendicular portion substantially perpendicular to the exterior surface and the sidewall further including a parallel portion extending from the perpendicular portion, the parallel portion extending from the perpendicular portion at an angle greater than about 90 degrees as measured with reference to the exterior surface.

2. The device of claim 1 wherein the parallel portion is substantially parallel to a lower surface of the recess.

3. The device of claim 1 further comprising a therapeutic agent disposed within the recess.

4. The device of claim 1 wherein the sidewall is formed of material skived from the surface to form the recess.

5. The device of claim 1 wherein the device is a stent stamped from a flat sheet of material forming a plurality of struts defining the exterior surface of the stent, the flat sheet having two longitudinal edges and designed to be joined together to form a cylindrical stent.

6. The device of claim 1 wherein the device is a stent consisting of a plurality of segments, each segment stamped from a flat sheet of material and bent into a sinusoidal ring to form struts of the stent, the sinusoidal ring having certain points defined as a peak deviation from a stent centerline and some of the points of one segment designed to be joined to some points of another segment to form the stent.

7. The device of claim 1 wherein the device is a stent consisting of a plurality of wires formed into struts which define the exterior surface of the stent and the wires being joined to form the stent.

8. The device of claim 1 further comprising:
at least one second sidewall on the exterior surface, the second sidewall separated from the first sidewall by the recess and connected to the first sidewall via a lower surface of the recess, each second sidewall protruding from the exterior surface substantially perpendicularly; and the second sidewall including a parallel portion extending from the perpendicular portion, the parallel portion extending from the perpendicular portion at an angle less than about 90 degrees as measured with reference to the exterior surface.

9. A system for treating a vascular condition, the system comprising:
a catheter; and
a stent carried on the catheter, the stent including an exterior surface on the device, at least one recess formed in the exterior surface, and at least one sidewall protruding from the exterior surface adjacent the at least one recess defining a channel with the recess into which the drug may be loaded, the sidewall including a perpendicular portion substantially perpendicular to the exterior surface and the sidewall further including a parallel portion extending from the perpendicular portion, the parallel portion extending from the perpendicular portion at an angle greater than about 90 degrees as measured with reference to the exterior surface.

10. The system of claim 9 wherein the parallel portion is substantially parallel to a lower surface of the recess.

11. The system of claim 9 further comprising a therapeutic agent disposed within the recess.

12. The system of claim 9 wherein the stent further comprises at least one second sidewall on the exterior surface, the second sidewall separated from the first sidewall by the recess and connected to the first sidewall via a lower surface of the recess, each second sidewall protruding from the exterior surface substantially perpendicularly; and the second sidewall including a parallel portion extending from the perpendicular portion, the parallel portion extending from the perpendicular portion at an angle less than about 90 degrees as measured with reference to the exterior surface.

* * * * *